United States Patent [19]

Kmetz et al.

[11] 4,085,079

[45] Apr. 18, 1978

[54] FORMALDEHYDE SOLUTIONS STABILIZED WITH INTERPOLYMERS OF VINYL ACETATE, VINYL ACETAL AND VINYL ALCOHOL

[75] Inventors: Richard C. Kmetz, Longmeadow; Leland P. Miner, Wilbraham, both of Mass.

[73] Assignee: Monsanto Company, St. Louis, Mo.

[21] Appl. No.: 764,784

[22] Filed: Feb. 2, 1977

[51] Int. Cl.² .............................................. C07C 47/04
[52] U.S. Cl. ...................... 260/29.6 B; 260/29.6 TA; 260/73 L; 260/606
[58] Field of Search .......... 260/606, 29.6 TA, 29.6 B, 260/73 L

[56] References Cited

U.S. PATENT DOCUMENTS

| | | | |
|---|---|---|---|
| 2,036,092 | 3/1936 | Morrison et al. | 260/73 R |
| 2,193,035 | 3/1940 | Matthews et al. | 260/73 L |
| 2,211,323 | 8/1940 | Fordyce | 260/73 L |
| 3,406,206 | 10/1968 | Locke | 260/29.6 ME |
| 3,518,313 | 6/1970 | Iida et al. | 260/606 |
| 3,816,539 | 6/1974 | Sanborn et al. | 260/606 |

FOREIGN PATENT DOCUMENTS

| | | | |
|---|---|---|---|
| 1,503,256 | 10/1967 | France | 260/606 |
| 968,762 | 9/1964 | United Kingdom | 260/606 |

*Primary Examiner*—Eugene C. Rzucidlo
*Attorney, Agent, or Firm*—R. Bruce Blance; William J. Farrington; James C. Logomasini

[57] ABSTRACT

A method of stabilizing concentrated aqueous formaldehyde solutions by the addition of a stabilizing amount of an interpolymer of vinyl acetate, vinyl acetal and vinyl alcohol to the formaldehyde solution. The interpolymer comprises from about 25 to about 65 parts by weight vinyl acetate units, from about 20 to about 72 parts by weight vinyl acetal units derived from acetaldehyde and from about 3 to about 15 parts by weight of vinyl alcohol units. The interpolymer is prepared by alcoholysis and acetalization of a low molecular weight polyvinyl acetate.

9 Claims, No Drawings

FORMALDEHYDE SOLUTIONS STABILIZED WITH INTERPOLYMERS OF VINYL ACETATE, VINYL ACETAL AND VINYL ALCOHOL

BACKGROUND OF THE INVENTION

1. Field of the Invention

This invention relates to stabilized formaldehyde solutions and a method of stabilizing formaldehyde solutions and in particular it relates to concentrated aqueous solutions stabilized with an interpolymer of vinyl acetate, vinyl acetal and vinyl alcohol and to a method of stabilizing aqueous formaldehyde solutions with the aforesaid interpolymer.

2. Description of the Prior Art

Aqueous solutions of formaldehyde are well-known in the art and various additives have been employed in an attempt to prepare and provide stabilized concentrated solutions of formaldehyde. Currently, when employing 37 percent solutions of formaldehyde in water, generally no stabilizer is necessary since at this concentration little or no formation of para-formaldehyde occurs. When preparing aqueous solutions of formaldehyde in excess of 37 percent such as 50 percent solutions of formaldehyde in water, it is necessary to keep the solution at a temperature of over 60° C. in order to prevent formation of para-formaldehyde. Even then the life of the solution is still somewhat limited to a period of hours. Various stabilizers have been proposed and used to prepare concentrated solutions. One common stabilizer is methanol. However, the actual concentration of formaldehyde in aqueous formaldehyde solutions is still limited when methanol is used as the stabilizer in small quantities and if greater quantities of methanol are employed to stabilize more concentrated solutions of formaldehyde in water, the methanol can be determinental to the preparation of satisfactory formaldehyde type thermosetting resins. Other stabilizers have been proposed but again the quantities necessary are quite large and have an adverse effect on their use in preparing thermosetting condensation resins such as phenol-formaldehyde, melamine-formaldehyde and urea-formaldehyde resins.

Recently, polyvinyl acetals have been investigated as stabilizers for aqueous formaldehyde solutions. The use of water insoluble formalin insoluble polyvinyl acetals as stabilizers has been described in combination with an anionic surface active agent used to stabilize the polyvinyl acetal. However, such surface active agents are undesirable because they can generate foaming problems in the aqueous formaldehyde solution, they can affect the properties of resin solutions derived from the aqueous formaldehyde such as the electrical resistance and moisture resistance and because the stabilizer concentrate of polyvinyl acetal and surfactant in water tends to be corrosive and to require special materials of construction.

A method of stabilizing a concentrated aqueous solution of formaldehyde with polyvinyl formal has been described in which the polyvinyl formal is dissolved in a concentrated solution of formaldehyde in aqueous methanol which is then added to the aqueous formaldehyde solution to stabilize it. In forming the stabilizer concentrate the aqueous formaldehyde and methanol is heated for a few hours at a temperature in the range of 130 to 190° F. Stabilization by this method is undesirable because the stabilizer concentrate tends to evolve irritating vapors of formaldehyde, because of the lengthy heating period and because of the poor storage stability and corrosiveness of the concentrate.

SUMMARY OF THE INVENTION

The present invention is directed to concentrated aqueous formaldehyde solutions stabilized with a polymer which is readily dissolved in a commercially available solvent particularly methanol which is a usual component of aqueous formaldehyde solutions and is easily added to the aqueous formaldehyde solution without the need for a heating step and without the presence of surfactants. The stabilized concentrated aqueous formaldehyde solutions show improved stability over aqueous formaldehyde solutions stabilized with polyvinyl formal and comprise a concentrated aqueous formaldehyde solution containing an interpolymer of vinyl acetate, vinyl acetal and vinyl alcohol wherein the interpolymer contains from about 25 to about 60 parts by weight vinyl acetate units, from about 20 to about 72 parts by weight of vinyl acetal units and from about 3 to about 15 parts by weight of vinyl alcohol units, and is derived from a polyvinyl acetate of weight average molecular weight in the range of about 2000 to about 60000 by alcoholysis and acetalization. The interpolymer concentration in the concentrated aqueous formaldehyde solution should be at least about 1 p.p.m.

Another aspect of the invention is directed to a process of stabilization of concentrated aqueous solutions of formaldehyde by addition thereto of a solution of the above described interpolymer in solution in an organic solvent to provide a concentration of at least about 1 p.p.m. by weight of the interpolymer in the aqueous formaldehyde.

PREFERRED EMBODIMENTS

The interpolymers which are used in the stabilization of concentrated aqueous solutions of formaldehyde comprise from about 25 to about 65 parts by weight vinyl acetate units, from about 20 to about 72 parts by weight vinyl acetal units derived from acetaldehyde and from about 3 to about 15 parts by weight of vinyl alcohol units. In a preferred embodiment the interpolymer comprises from about 30 to about 50 parts by weight vinyl acetate units, from about 40 to about 67 parts by weight vinyl acetal units and from about 3 to about 10 parts by weight vinyl alcohol units.

The interpolymers are prepared from relatively low molecular weight polyvinyl acetate of weight average molecular weight in the range of from about 2000 to about 60000. More preferably, the polyvinyl acetate has a weight average molecular weight in the range of about 6000 to about 20,000 since such polyvinyl acetates can be conveniently prepared by free radical polymerization without the need for excessive amounts of initiator and chain transfer agents and provide resin solutions of relatively low viscosity for ease of handling without the need for excessive amounts of solvent.

The polyvinyl acetate resins are dissolved in a low boiling alcohol selected from the group consisting of methanol, ethanol, propanol and isopropyl alcohol. Acetaldehyde is added and the polyvinyl acetate is subjected to alcoholysis and acetalization in the presence of a strong acid catalyst. The amounts of alcohol and acetaldehyde, the ratio of alcohol to acetaldehyde and the time and temperature of the alcoholysis and acetalization reactions are readily selected, within the skill in the art to obtain an interpolymer containing the desired ratio of vinyl acetate, vinyl acetal and vinyl alcohol. While the alcoholysis and acetalization are conveniently carried out concurrently, they may also be carried out sequentially. The acid catalyst can be any acid with a pKa at 25° C. of at least about 2.0. The strong mineral acids such as sulfuric acid and hydrochloric are generally preferred.

When the desired degree of alcoholysis and acetalization have been achieved, the reaction solution is treated with an alkali or alkaline earth metal oxide, hydroxide, carbonate, bicarbonate or salt of a low boiling organic acid to neutralize the strong acid catalyst. Salts such as sodium propionate and potassium acetate are suitable. The interpolymer solution is then dried to remove the alcohol solvent, is washed repeatedly with water to remove inorganic salts and is again dried. The dried interpolymer is then dissolved in a suitable water soluble neutral or basic organic solvent to provide a stabilizer solution for the aqueous formaldehyde solution. Such solvents include the lower aliphatic alcohols, ketones, amines, amides, and ethers. A preferred solvent is methanol since the interpolymer is readily soluble in it and since methanol is generally present as a minor component of aqueous formaldehyde, its use as the solvent of the stabilizing solution does not add an additional component to the formaldehyde. A particular advantage of the interpolymer stabilizer of the present invention is found in the fact that it dissolves readily in methanol at room temperature without requiring a heat treatment in the presence of formaldehyde in the fashion taught in the prior art for polyvinyl formal. The stabilizing solution of interpolymer can contain up to 40 weight percent interpolymer. However, for ease of metering without introducing excessive amounts of methanol into the aqueous formaldehyde, the concentration of interpolymer is preferably in the range of about 0.5 to about 5 weight percent.

The stabilizing solution can be used to increase the stability of aqueous formaldehyde solutions against the formation of paraformaldehyde which is manifested in varying degrees as a haze, as a precipitate, as beads or strings and finally as a solid block deposited on the bottom and walls of the formaldehyde container. The stability of solutions containing less than about 37 weight percent formaldehyde is generally adequate at 25° C. without stabilizer added to the solution. The interpolymer is effective, however, as a stabilizer of solutions containing at least about 37 weight percent formaldehyde and as high as about 70 weight percent formaldehyde and is generally effective in reducing the storage temperature necessary to suppress paraformaldehyde formation.

The interpolymer solution in an organic solvent, preferably methanol, is added to the aqueous formaldehyde solution in an amount to produce a concentration of interpolymer in the aqueous solution in the range of about 1 to about 200 p.p.m., preferably about 5 to about 100 p.p.m. and more preferably about 10 to about 50 p.p.m.

The following examples are set forth to illustrate the invention but are not to be construed as limiting the scope thereof. All parts and percentages are by weight unless indicated otherwise.

EXAMPLE 1

1000 Parts by weight of a polyvinyl acetate of weight average molecular weight of 10,000 is dissolved in 540 parts of methanol contained in a stainless steel kettle and 300 parts of acetaldehyde is added thereto and mixed thoroughly. The solution is slowly agitated and a solution of 92 parts of sulfuric acid in 80 parts of methanol is added in approximately 20 minutes. The kettle is sealed and heated to 60° C. and a pressure of 2000 g. per sq. cm. for 30 minutes. Thereafter, the kettle is cooled to room temperature and the sulfuric acid is neutralized by addition of potassium acetate. Solvent is stripped from the solution and the polymeric residue is washed three times by stirring it with equal volumes of hot water and decanting the water after each wash. The interpolymeric residue is then dried and dissolved in methanol to provide a 20 weight percent solution. The interpolymer contains 75 weight percent vinyl acetate, 5 weight percent vinyl alcohol and 20 weight percent vinyl acetal.

EXAMPLES 2 – 6

A series of interpolymers of vinyl acetate, vinyl acetal and vinyl alcohol are prepared by the method set forth in Example 1. In Examples 2–5, the initial polyvinyl acetate is the same as in Example 1 and the period of heating in the presence of acetaldehyde and methanol is varied to provide interpolymers containing different degrees of acetalization. In Example 6, the polyvinyl acetate has a weight average molecular weight of approximately 45,000 and is subjected to acetalization for 4.5 hours. The data for the examples are presented in Table 1.

TABLE 1

Interpolymers of Vinyl Acetate, Vinyl Acetal and Vinyl Alcohol

| Example | Initial PVAc- Mw | Interpolymer, Weight % | | |
|---|---|---|---|---|
| | | Vinyl Acetate | Vinyl Acetal | Vinyl Alcohol |
| 1 | 10,000 | 75 | 20 | 5 |
| 2 | 10,000 | 45 | 49 | 6 |
| 3 | 10,000 | 34 | 58 | 8 |
| 4 | 10,000 | 27 | 64 | 9 |
| 5 | 10,000 | 19 | 70 | 11 |
| 6 | 45,000 | 45 | 49 | 6 |

Examples 1–5 are subjected to accelerated stabilization tests. The interpolymer solutions are diluted to 2 weight percent solutions with methanol and metered quantities are added to 50 weight percent aqueous formaldehyde solution to provide samples containing 10 and 20 parts of interpolymer per million parts of formaldehyde solution. The solutions are maintained at 30° C. and are observed for the development of haze. The time in minutes for the solution to develop a haze equivalent to a 25 APHA turbidity standard is noted. The data are presented in Table 2. Examples 2–4 are within the scope of the present invention. Examples 1 and 5 which demonstrate a significantly poorer stabilization effect are outside the scope of the invention. Example 7 also presented for comparative purposes is a polyvinyl formal stabilizer of a prior art teaching.

TABLE 2

ACCELERATED STABILIZATION TEST: 50% AQUEOUS FORMALDEHYDE. 30° C.

| Stabilizer | Time for Haze to equal 25 APHA Standard, Mins. | |
|---|---|---|
| | 10 p.p.m. | 20 p.p.m. |
| Ex. 1 | 80 | 123 |
| Ex. 2 | 239 | 351 |
| Ex. 3 | 220 | 388 |
| Ex. 4 | 180 | — |
| Ex. 5 | 147 | — |
| Polyvinyl (Ex. 7) formal | 160 | 200 |

A storage test is carried out at 25° C. with the interpolymer of Example 6 added to an aqueous formaldehyde solution containing 44 weight percent formaldehyde to provide an interpolymer concentration of 10 p.p.m. No haze develops within 90 days. In contrast, a commercial aqueous formaldehyde solution containing 10 ppm of a prior art stabilizer forms haze within 1 day and is a solid mass after 90 days.

What is claimed is:

1. A process of stabilizing an aqueous formaldehyde solution comprising dissolving an interpolymer of vinyl acetate, vinyl alcohol and vinyl acetal in an organic solvent and admixing the solution of the interpolymer with the formaldehyde solution to form a stabilized formaldehyde solution containing at least 1 p.p.m. of the interpolymer by weight, wherein the interpolymer comprises from about 25 to about 65 parts by weight of vinyl acetate units, from 3 to about 15 parts by weight of vinyl alcohol units and from about 20 to about 72 parts by weight of vinyl acetal units and wherein the interpolymer is the alcoholysis and acetalization product of a polyvinyl acetate of weight average molecular weight in the range of about 2000 to about 60000.

2. The process of claim 1 wherein the interpolymer comprises from about 30 to about 50 parts by weight of vinyl acetate units, from about 3 to about 10 parts by weight of vinyl alcohol units and from about 40 to about 67 parts by weight of vinyl acetal units.

3. The process of claim 2 wherein the weight average molecular weight of the polyvinyl acetate is in the range of about 6000 to about 20,000.

4. The process of claim 1 wherein the organic solvent is methanol.

5. The process of claim 1 wherein the concentration of formaldehyde in the aqueous formaldehyde solution is in the range of about 37 to about 70 weight percent.

6. An aqueous formaldehyde solution containing at least about 37 weight percent of formaldehyde and at least about 1 p.p.m. by weight of an interpolymer comprising from about 25 to about 65 parts by weight of vinyl acetate units, from about 3 to about 15 parts by weight of vinyl alcohol units and from about 20 to about 72 parts by weight of vinyl acetal units and wherein the interpolymer is the alcoholysis and acetalization product of a polyvinyl acetate of weight average molecular weight in the range of about 2000 to about 60,000.

7. The formaldehyde solution of claim 6 wherein the interpolymer comprises from about 30 to about 50 parts by weight of vinyl acetate units, from about 3 to about 10 parts by weight of vinyl alcohol units and from about 40 to about 67 parts by weight of vinyl acetal units.

8. The formaldehyde solution of claim 7 wherein the weight average molecular weight of the polyvinyl acetate is in the range of about 6000 to about 20,000.

9. The formaldehyde solution of claim 8 wherein the concentration of formaldehyde in the aqueous formaldehyde solution is in the range of about 37 to about 70 weight percent.

* * * * *

Disclaimer 4,085,079.—*Richard C. Kmetz*, Longmeadow and *Leland P. Miner*, Wilbraham, Mass. FORMALDEHYDE SOLUTIONS STABILIZED WITH INTERPOLYMERS OF VINYL ACETATE, VINYL ACETAL AND VINYL ALCOHOL. Patent dated Apr. 18, 1978. Disclaimer filed June 14, 1982, by the assignee, *Monsanto Co.*

Hereby enters this disclaimer to claims 1, 4, 5, and 6 of said patent.

[*Official Gazette August 10, 1982.*]